(12) United States Patent
Simpson et al.

(10) Patent No.: US 9,545,454 B2
(45) Date of Patent: *Jan. 17, 2017

(54) S100B MINI-PROMOTERS (71) Applicant: The University of British Columbia, Vancouver (CA)

(72) Inventors: Elizabeth M. Simpson, Vancouver (CA); Charles de Leeuw, Seattle, WA (US); Wyeth W. Wasserman, Vancouver (CA); Daniel Goldowitz, Port Moody (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,013

(22) Filed: Jul. 24, 2015

(65) Prior Publication Data
US 2016/0030597 A1  Feb. 4, 2016

Related U.S. Application Data (60) Provisional application No. 62/031,453, filed on Jul. 31, 2014.

(51) Int. Cl.
*A61K 48/00* (2006.01)
*C12N 15/85* (2006.01)
*C12N 15/86* (2006.01)

(52) U.S. Cl.
CPC .......... *A61K 48/0058* (2013.01); *C12N 15/85* (2013.01); *C12N 15/86* (2013.01); *C12N 2750/14143* (2013.01); *C12N 2830/008* (2013.01); *C12N 2830/85* (2013.01)

(58) Field of Classification Search
None
See application file for complete search history.

(56) References Cited

U.S. PATENT DOCUMENTS 8,895,715 B2 * 11/2014 Simpson ................ C07K 14/47 435/320.1
2009/0280568 A1 * 11/2009 Simpson ................ C07K 14/47 435/455

* cited by examiner

*Primary Examiner* — Antonio Galisteo Gonzalez
(74) *Attorney, Agent, or Firm* — Pamela J. Sherwood; Bozicevic, Field & Francis LLP (57) ABSTRACT

Isolated polynucleotides comprising a S100B mini-promoters are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, gene therapy, etc.

10 Claims, 2 Drawing Sheets
(2 of 2 Drawing Sheet(s) Filed in Color)

Figure 1

Ple266-icre (*S100B* RRs) in ssAAV9 virus vEMS51

SEQUENCE LISTING

```
<160> NUMBER OF SEQ ID NOS: 3

<210> SEQ ID NO 1
<211> LENGTH: 2982
<212> TYPE: DNA
<213> ORGANISM: Homo sapiens

<400> SEQUENCE: 1
cagatgtgag ttaagcagtt tgaacaatcg attgattaga cttttgtggc tgctcatttg      60
ggcatgtggc cgagtactgt gctgtcctgg cccacagcgt cctacaggaa gggacgggct     120
gtaagacgtg ggatcttctg aagtcgtcaa atgaaaaaca ctcctgttga gtgaaaaaac     180
aaataggcta atcctatgat tttttaaaca tttaaacctg acatgatttt attgcaaatt     240
tccaagaatc cttaaaagtt ataaaaagca taatcaaaat aaatatctgt gacagagttc     300
tacaaaaggg aaaactcagt tttccttttg agatcttgcc ccagcatcag ttcaaacact     360
tcctcatata tttcaccaag actcagttcc tgagcaagaa accacaggca cagcaagtgc     420
catgaaaagc ggctttgtgt ggggtgggct cttcacactc caatctccac ttccttctca     480
aggcctcaaa aaaagttgaa aaatgaaaac aaaagccctg ctgtgttgag ctgggctctg     540
gcgttgccat ggacccaggg caaacagcgg tgctcctgct ctgccccgg ctcagctcat     600 gctgggcctg cacttctgga agggagcatg gactttggaa tgactggtta gaacccaaat     660
gaattaatgg aatttgacat agttcaaaaa taataaaatg tgatacccat gaaatgctga     720
tattctgcct taatttgcca gattggggc ctcctggatt tagagtattc taaagtagcc     780
agtaggttca ctctgccctt ttagacctaa tatatctggc tcagaaagaa gtctctgtcc     840
ctctgctatt tgctgttctt tgctttgccc agtctgactc ctgccagctc caggttctgc     900
agacaagaac agtaacttt ataataataa taatgactcc caagtgagtg cattgggccc     960
ttcacgtgtg tctgtatgtg tgcacatgta tgtgcgtgtc aatttccttt actcctccta    1020
cagccctctc aggggtgcag ctttttttct gtcttttact cagcctgaga aaggttgtcg    1080
tttgacaagg tttgttcaga ggtcggatct gaatccagct ccaaggcccc agcacccaag    1140
ccctgacccc atgctgcct gctggctggg agtggcattc tttagaacag gaaaggcagt    1200
gagttctcat tgcatcaata cttgcatttg ctacaacaga agcttttgt ctcttcctca    1260 cattccttta gaacacaagc ctcctttct gcctgtggcc atcggtcact ggagtcagcc    1320
tcgtgagtgg cttggtggcg gatggcaccg tcctttgtgg gagaaaacaa tgttgctgcc    1380
caggcctttc tggaatgacc ccttcccacc ccctgaccag ccccagcaag gcccggggct    1440
ggctgcctag ttgattggag ccaagagttt gctgaatgga tgaagggaga agggacatcc    1500
```

| | |
|---|---:|
| aagtgactga agaagatctt aacagaagat tgatatattc aaatagaggc ccctgttgac | 1560 |
| ccacaagctc cttcgtgctc tggcctgggc aggcagcgtg gtcagcactt acaggaatgg | 1620 |
| tccctccaac atctgagcga ggaaggggca cagagcacag ttgtgccttc cttgggcctg | 1680 |
| ggcaagctct gtgcttcaca gagcaagcct gtgtcagatc cttcagcaga gaccacagcc | 1740 |
| aggggtggtg aagccgatga ggaagtgagg gccaaccaca ctgctcaggc tgttcctcac | 1800 |
| aggaggctgg ggcaggctga gccacgcaag accacagctc tcagccctgt gctatttcca | 1860 |
| gggcacactt acagatcctg aatggtagag aacgtcctgg ataaaacaat gacagcaaga | 1920 |
| cagccatgta cacagatatc ttgtgggaaa ccctttcacg ccactttga aactgggttg | 1980 |
| ggagaaggac gtgatgctgg gtcaggcatc cattgggac catggacatt tttggagagt | 2040 |
| ttgggccaat gttcttgtgt aatttgtcag aaggaacacc tacttcttca ttcttgtgaa | 2100 |
| gaagaaccca taaactggcc cccgtgttca gaggctccag tcgagcgagt tgaggggaca | 2160 |
| gctggacttc tccttcctca ggctggctgg aggcttcagc aagggggcac accgtccaca | 2220 |
| cgcctctgta aaacagcgtt cgaacgggac atctctaagg catcgtccaa ctctgagagt | 2280 |
| ctgtgacctt ccaccctggg gtggaggaa aggccttggg atacagtcca cacatcacgt | 2340 |
| tttcccctaa aagtaccacc cgttttagtc cctgcagaca ctggcctcag cagcttctct | 2400 |
| gaggcagccc cgttgagccc agggctgacc acagacaagc actactgtcc acagaacttc | 2460 |
| acgcccagtg gggccagact tggaggatgg cagaggagag aagctccagg ggcctctcca | 2520 |
| ttagaaacca acttgcaggc cacttaatct cctatgctca gcctgtactt ggaagctgct | 2580 |
| tgttcttggc tgcacatttg ctttgtttga atcaattaat ccaagtctct ctcctctccc | 2640 |
| cacccccaac cttgccttta gggtgacatc aatattcatg taataaagaa atcgcacaaa | 2700 |
| aagctgactc cccacttcct gccctacagg ccctttttc ttcctcagcc catgtgcaat | 2760 |
| cctggctccc agcaagtccc cggggctgct tggtcaatgc agcccgtgt gcaggcctgg | 2820 |
| cagccctgcc accccgcct tcggctccca ttggctgcca cggcctgcag tgggctgcac | 2880 |
| cagggttcat ccatcctccc tgggcagagg gaataagagg ctgcctctgc ccaccagtcc | 2940 |
| tgccgcccag gacccgcagc agagacgacg cctgcagcaa gg | 2982 |

<210> SEQ ID NO 2
<211> LENGTH: 1385
<212> TYPE: DNA
<213> ORGANISM: Homo sapiens

<400> SEQUENCE: 2

| | |
|---|---:|
| gtggtcagca cttacaggaa tggtccctcc aacatctgag cgaggaaggg gcacagagca | 60 |
| cagttgtgcc ttccttgggc ctgggcaagc tctgtgcttc acagagcaag cctgtgtcag | 120 |
| atccttcagc agagaccaca gccaggggtg gtgaagccga tgaggaagtg agggccaacc | 180 |
| acactgctca ggctgttcct cacaggaggc tggggcaggc tgagccacgc aagaccacag | 240 |
| ctctcagccc tgtgctattt ccagggcaca cttacagatc ctgaatggta gagaacgtcc | 300 |
| tggataaaac aatgacagca agacagccat gtacacagat atcttgtggg aaacccttc | 360 |
| acggccactt tgaaactggg ttgggagaag gacgtgatgc tgggtcaggc atccattggg | 420 |
| gaccatggac attttggag agtttgggcc aatgttcttg tgtaatttgt cagaaggaac | 480 |
| acctacttct tcattcttgt gaagaagaac ccataaactg gccccgtgt tcagaggctc | 540 |
| cagtcgagcg agttgagggg acagctggac ttctccttcc tcaggctggc tggaggcttc | 600 |
| agcaagggg cacaccgtcc acacgcctct gtaaaacagc gttcgaacgg gacatctcta | 660 |

```
aggcatcgtc caactctgag agtctgtgac cttccaccct ggggtggagg gaaaggcctt       720
gggatacagt ccacacatca cgttttcccc taaaagtacc acccgtttta gtccctgcag       780
acactggcct cagcagcttc tctgaggcag ccccgttgag cccagggctg accacagaca       840
agcactactg tccacagaac ttcacgccca gtggggccag acttggagga tggcagagga       900
gagaagctcc aggggcctct ccattagaaa ccaacttgca ggccacttaa tctcctatgc       960
tcagcctgta cttggaagct gcttgttctt ggctgcacat ttgctttgtt tgaatcaatt      1020
aatccaagtc tctctcctct ccccaccccc aaccttgcct ttagggtgac atcaatattc      1080
atgtaataaa gaaatcgcac aaaaagctga ctccccactt cctgccctac aggccctttt      1140
ttcttcctca gcccatgtgc aatcctggct cccagcaagt ccccggggct gcttggtcaa      1200
tgcagccctg tgtgcaggcc tggcagccct gccaccccg ccttcggctc ccattggctg       1260
ccacggcctg cagtgggctg caccaggggtt catccatcct ccctgggcag agggaataag     1320
aggctgcctc tgcccaccag tcctgccgcc caggacccgc agcagagacg acgcctgcag      1380
caagg                                                                  1385

<210> SEQ ID NO 3
<211> LENGTH: 1597
<212> TYPE: DNA
<213> ORGANISM: Homo sapiens

<400> SEQUENCE: 3
cagatgtgag ttaagcagtt tgaacaatcg attgattaga cttttgtggc tgctcatttg        60
ggcatgtggc cgagtactgt gctgtcctgg cccacagcgt cctacaggaa gggacgggct       120
gtaagacgtg ggatcttctg aagtcgtcaa atgaaaaaca ctcctgttga gtgaaaaaac       180
aaataggcta atcctatgat ttttttaaaca tttaaacctg acatgatttt attgcaaatt      240
tccaagaatc cttaaaagtt ataaaaagca taatcaaaat aaatatctgt gacagagttc       300
tacaaaaggg aaaactcagt tttccttttg agatcttgcc ccagcatcag ttcaaacact       360
tcctcatata tttcaccaag actcagttcc tgagcaagaa accacaggca cagcaagtgc       420
catgaaaagc ggctttgtgt ggggtgggct cttcacactc caatctccac ttccttctca       480
aggcctcaaa aaaagttgaa aaatgaaaac aaaagccctg ctgtgttgag ctgggctctg       540
gcgttgccat ggacccaggg caaacagcgg tgctcctgct ctgcccccgg ctcagctcat       600
gctgggcctg cacttctgga agggagcatg gactttggaa tgactggtta gaacccaaat       660
gaattaatgg aatttgacat agttcaaaaa taataaaatg tgatacccat gaaatgctga       720
tattctgcct taatttgcca gattgggggc ctcctggatt tagagtattc taaagtagcc       780
agtaggttca ctctgccctt ttagacctaa tatatctggc tcagaaagaa gtctctgtcc       840
ctctgctatt tgctgttctt tgctttgccc agtctgactc ctgccagctc caggttctgc       900
agacaagaac agtaactttt ataataataa taatgactcc caagtgagtg cattgggccc       960
ttcacgtgtg tctgtatgtg tgcacatgta tgtgcgtgtc aatttccttt actcctccta      1020
cagccctctc aggggtgcag cttttttttct gtctttact cagcctgaga aaggttgtcg       1080
tttgacaagg tttgttcaga ggtcggatct gaatccagct ccaaggcccc agcacccaag      1140
ccctgacccc atggctgcct gctggctggg agtggcattc tttagaacag gaaaggcagt      1200
gagttctcat tgcatcaata cttgcatttg ctacaacaga agcttttgt ctcttcctca      1260 cattccttta gaacacaagc ctcctttttct gcctgtggcc atcggtcact ggagtcagcc      1320
```

-continued

```
tcgtgagtgg cttggtggcg gatggcaccg tcctttgtgg gagaaaacaa tgttgctgcc    1380
caggcctttc tggaatgacc ccttcccacc ccctgaccag ccccagcaag gcccggggct    1440
ggctgcctag ttgattggag ccaagagttt gctgaatgga tgaagggaga agggacatcc    1500
aagtgactga agaagatctt aacagaagat tgatatattc aaatagaggc ccctgttgac    1560
ccacaagctc cttcgtgctc tggcctgggc aggcagc                             1597
```

S100B MINI-PROMOTERS

FIELD OF THE INVENTION

The invention relates to gene promoters and regulatory elements. More specifically, the invention relates to novel S100B promoter compositions and related methods.

BACKGROUND

The S100 calcium binding protein B gene (S100B) encodes the S100B Protein which is expressed and secreted by glial cells and astrocytes of the brain (Vives et al. 2003). The overexpression of the S100B protein has been associated with the neurodegeneration in Alzheimer's Disease (Leclerc E et al. 2010) and Parkinson Disease (Sathe K et al. 2012). Furthermore, serum level alterations of the S100B protein have been reported as a potential biomarker for a variety of disease indications including arterial hypertension (Gruden M A et al. 2014), preeclampsia (Bergman et al. 2014) and traumautic brain injury (Yokobori S et al. 2013).

There is a need for characterized human S100B promoters for gene expression, for instance in human gene therapy applications. It is particularly useful to identify small promoter elements that are sufficient to drive expression in regions of the brain, for instance in the glial cells or astrocytes in the central nervous system as well as in Müller glia in the retina. Such small promoter elements, or "mini-promoters" are particularly useful in certain applications, for instance they are more amenable to insertion into viral vectors used in gene therapy applications.

S100B promoter elements described in the art, including:

Dagdan E, Morris D W, Campbell M, Hill M, Rothermundt M, Kästner F, Hohoff C, von Eiff C, Krakowitzky P, Gill M, McKeon P, Roche S. Functional assessment of a promoter polymorphism in S100B, a putative risk variant for bipolar disorder. Am J Med Genet B Neuropsychiatr Genet. 2011 September; 156B(6):691-9.

Pustylnyak V O, Lisachev P D, Shtark M B, Epstein O I. Regulation of S100B gene in rat hippocampal CA1 area during long term potentiation. Brain Res. 2011 Jun. 7; 1394:33-9.

Geller S F, Ge P S, Visel M, Flannery J G. In vitro analysis of promoter activity in Müller cells. Mol Vis. 2008 Apr. 23; 14:691-705.

US2009-0280568 A1 describes earlier S100B mini-promoters designs by the inventors.

SUMMARY OF THE INVENTION

The present invention provides novel nucleic acid sequence compositions and methods relating to minimal human S100B promoters. The invention is based in part on the surprising discovery that certain minimal S100B promoter elements are capable of expressing in specific cell types, for instance in cells of the brain.

In one embodiment of the invention, there is provided an isolated nucleic acid fragment comprising a S100B mini-promoter, wherein the S100B mini-promoter comprises a S100B regulatory element operably linked in a non-native conformation to a S100B basal promoter. The S100B mini-promoter may have a nucleic acid sequence which is substantially similar in sequence and function to SEQ ID NO: 1. The S100B basal promoter may have a nucleic acid sequence which is substantially similar in sequence and function to SEQ ID NO: 2. The S100B regulatory element may have a nucleic acid sequence which is substantially similar in sequence and function to SEQ ID NO: 3. In other embodiments, there is provided an isolated nucleic acid fragment comprising a S100B mini-promoter, wherein the S100B mini-promoter comprises a S100B basal promoter. The S100B basal promoter may have a nucleic acid sequence which is substantially similar in sequence and function to SEQ ID NO: 2. The S100B mini-promoters may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising a S100B mini-promoter, wherein the S100B mini-promoter comprises a S100B regulatory element operably linked in a non-native conformation to a S100B basal promoter. The S100B mini-promoter may have a nucleic acid sequence which is substantially similar in sequence and function to SEQ ID NO: 1.

The S100B basal promoter may have a nucleic acid sequence which is substantially similar in sequence and function to SEQ ID NO: 2. The S100B regulatory element may have a nucleic acid sequence which is substantially similar in sequence and function to SEQ ID NO: 3. In other embodiments, there is provided an expression vector comprising a S100B mini-promoter, wherein the S100B mini-promoter comprises a S100B basal promoter. The S100B basal promoter may have a nucleic acid sequence which is substantially similar in sequence and function to SEQ ID NO: 2. The S100B mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell an expression vector comprising a S100B mini-promoter element, wherein the S100B mini-promoter element comprises a S100B regulatory element operably linked in a non-native conformation to a S100B basal promoter element. In another embodiment, the S100B mini-promoter comprises a S100B basal promoter. Cells of interest include, without limitation, cells of the peripheral or central nervous system and progenitors thereof, e.g. embryonic stem cells, neural stem cells, neurons, glial cells, astrocytes, microgial cells, etc. The S100B mini-promoter may have a nucleic acid sequence which is substantially similar in sequence and function to SEQ ID NO: 1. The S100B regulatory element may have a nucleic acid sequence which is substantially similar in sequence and function to SEQ ID NO: 3. The S100B basal promoter may have a nucleic acid sequence which is substantially similar in sequence and function to SEQ ID NO: 2. The S100B mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a S100B mini-promoter element, wherein the S100B mini-promoter element comprises a S100B regulatory element operably linked in a non-native conformation to a S100B basal promoter element, and wherein the expressible sequence comprises a reporter gene. In other embodiments, the S100B mini-promoter comprises a S100B basal promoter. The S100B mini-promoter element may have a nucleic acid sequence substantially similar in sequence and function to SEQ ID NO: 1. The S100B regulatory element may have a nucleic acid sequence substantially similar in sequence and function to SEQ ID NO: 3. The S100B basal promoter element may have a nucleic acid sequence substantially similar in sequence and function to SEQ ID NO: 2. In some embodiments, the cell is a peripheral or central nervous system cell or progenitors thereof, including, without limitation, embryonic stem cells, neural stem cells, glial cells, astrocytes, neurons and the like etc. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a S100B mini-promoter element operably linked to an expressible sequence, wherein the S100B mini-promoter element comprises a S100B regulatory element operably linked in a non-native conformation to a S100B basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the S100B mini-promoter comprises a S100B basal promoter. The S100B mini-promoter element may have a nucleic acid sequence substantially similar in sequence and function to SEQ ID NO: 1. The S100B regulatory element may have a nucleic acid sequence substantially similar in sequence and function to SEQ ID NO: 3. The S100B basal promoter element may have a nucleic acid sequence substantially similar in sequence and function to SEQ ID NO: 2. In some embodiments, the cell is a peripheral or central nervous system cell or progenitors thereof, including, without limitation, embryonic stem cells, neural stem cells, glial cells, neurons and the like.

In certain embodiments of the invention, there is thus provided a method of treatment of a subject having a disease involving glial cells, the method comprising administering to the subject a therapeutically effective dose of a composition comprising a S100B mini-promoter element, wherein the S100B mini-promoter element comprises a S100B regulatory element operably linked in a non-native conformation to a S100B basal promoter element. In another embodiment, the S100B mini-promoter comprises a S100B basal promoter. The S100B mini-promoter element may have a nucleic acid sequence substantially similar in sequence and function to SEQ ID NO: 1. The S100B regulatory element may have a nucleic acid sequence substantially similar in sequence and function to SEQ ID NO: 3. The S100B basal promoter element may have a nucleic acid sequence substantially similar in sequence and function to SEQ ID NO: 2. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy, neuroinflammation, astrogliosis, multiple sclerosis, Parkinson's disease, Alzheimer's disease, aging, traumatic brain injury.

SHORT DESCRIPTION OF FIGURES

The patent or application file contains at least one drawing executed in color. Copies of this patent or patent application publication with color drawing(s) will be provided by the Office upon request and payment of the necessary fee.

FIG. 2A-2E—Ple266 (S100B RRs) expresses in glia of the brain and eye. The Ple266 promoter driving iCre expression was constructed and ssAAV9 virus generated (vEMS51). P0 mice were injected intravenously with virions and mice were harvested at P21 and P56 via perfusion and stained overnight for lacZ activity (blue), indicative of promoter activity. (FIG. 2A) a cryosection of the P21 brain demonstrates puffy processes associated with astrocyte morphology in both the cortex and hippocampus (arrows). (FIG. 2B) co-labeling of the astrocyte marker, Gfap, and X-gal staining indicates promoter activity in some astrocytes (arrows). (FIG. 2C) a 1-mm section demonstrating Bergmann glia fiber-staining in the cerebellum (arrows). (FIG. 2D) staining was observed in the trabecular meshwork of the eye (arrow). (FIG. 2E) in the retina, there are characteristic Müller glia staining (cell bodies in the INL; black arrows) and staining in the astrocytic layer just above the GCL (grey arrow). Cb, cerebellum; Ctx, cortex; GCL, ganglion cell layer; Hipp, hippocampus; INL, inner nuclear layer; ONL, outer nuclear layer; P, post-natal day; RR, regulatory regions.

DETAILED DESCRIPTION

The compositions of the present invention include novel polynucleotides comprising S100B promoter elements (also referred to herein as S100B mini-promoters) as well as novel expression vectors comprising said S100B promoter elements (or mini-promoters). The present invention also includes various methods utilizing these novel S100B promoter (or mini-promoter) elements or expression vectors.

Composition:

A "composition", such an a promoter, according to this invention refers to the combination of two or more sequences as described herein for co-administration or administration as part of the same structure.

Comprising:

A composition or method described herein as "comprising" one or more named elements, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

The term 'S100B' refers to the gene which encodes the S100 calcium binding protein B protein, other aliases include S100-beta. The human homolog of S100B is encoded by the human gene identified as EntrezGene #6285 and is located on chromosome 21 at location 21q22.3. The protein encoded by human S100B has the Protein Accession NP_006263.1 however other protein accession numbers may also be assigned to this protein. S100B may also include other isoforms and/or splice variants. Other mammalian S100B homologs may include but are not limited to: *Rattus norvegicus* (EntrezGene #25742), *Mus musculus* (EntrezGene #20203), *Pan troglodytes* (EntrezGene # #474141) and *Macaca mulatta* (EntrezGene #708117).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'S100B basal promoter', in the context of the present invention and as used herein, is a nucleic acid compound having a sequence with at least 65%, at least 70%, at least. 80%, at least 85%, at least 90%, at least 95%, or at least 99% similarity to SEQ ID NO: 2.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'S100B regulatory element', in the context of the present invention and as used herein, is a nucleic acid compound having a sequence with at least 65%, at least 70%, at least 80%, at least 85%, at least 90%, at least 95%, or at least 99% similarity to SEQ ID NO:5-7. The present invention provides, in certain embodiments as described herein, different promoters of the S100B gene. In some embodiments, the S100B promoter comprises a S100B regulatory element operably linked to a S100B basal promoter.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel S100B mini-promoters comprising a S100B regulatory element operably linked in a non-native conformation to a S100B basal promoter. In general the spacing between the S100B regulatory element and the S100B basal promoter is not more than about 15 KB, generally not more than about 10 KB, usually not more than about 1 KB, more often not more than about 500 nt, and may be not more than about 100 nt, down to a direct joining of the two sequences. In other embodiments, there is provided a minimal S100B basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art. In some embodiments of the invention, the expression sequence may include genome editing proteins such as zinc finger nucleases (ZFNs), transcription activator-like effector nucleases (TALENs) or clustered regularly interspaced short palindromic repeats enzymes (CRISPRs) or encode guide RNAs for such purposes.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds.

Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention.

Introduction of nucleic acids or expression vectors into cells may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

In certain embodiments of the invention, there are provided methods of treatment using the nucleic acids or expression vectors, for instance for gene therapy applications. The nucleic acids or expression vectors of the present invention may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenous, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

S100B Mini-Promoters

The present invention herein provides novel S100B mini-promoter sequences which are capable of effecting transcriptional expression in a spatial and temporal fashion in the brain or the eye. Certain S100B mini-promoters of the invention comprise minimal S100B promoter elements joined in a non-native configuration, thus providing advantageous characteristics. Other S100B mini-promoters of the invention comprise a minimal S100B basal promoter. Also provided are novel expression vector compositions comprising S100B mini-promoters which allow consistent specific spatiotemporal transcription of expression sequences. Also provided are novel methods utilizing these S100B mini-promoters and expression vectors.

The S100B promoters of the invention, as described herein, are referred to as 'mini-promoters' to reflect the fact that the mini-promoters comprise minimal S100B promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance a human S100B regulatory element corresponding to SEQ ID NO: 3 and the human S100B basal promoter elements corresponding to SEQ ID NO: 2 or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that human S100B mini-promoters having a sequence corresponding to SEQ ID NO: 1 (also referred to in the Working Examples as Ple266), and which are comprised of one human S100B regulatory elements operably linked in a non-native conformation to a human S100B basal promoter having a nucleic acid sequence corresponding to SEQ ID NO: 2, is capable of directing expression of an expressible sequence which is operably linked downstream of the S100B promoter in specific cell types in different regions of the brain and/or eye. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO: 1, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1-3 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

In one embodiment of the invention, there is provided an isolated nucleic acid fragment comprising a S100B mini-promoter, wherein the S100B mini-promoter comprises a S100B regulatory element operably linked in a non-native conformation to a S100B basal promoter. The S100B mini-promoter may have a nucleic acid sequence which is substantially similar in sequence and function to SEQ ID NO: 1. The S100B basal promoter may have a nucleic acid sequence which is substantially similar in sequence and function to SEQ ID NO: 2. The S100B regulatory element may have a nucleic acid sequence which is substantially similar in sequence and function to SEQ ID NO: 3. In other embodiments, there is provided an isolated nucleic acid fragment comprising a S100B mini-promoter, wherein the S100B mini-promoter comprises a S100B basal promoter. The S100B basal promoter may have a nucleic acid sequence which is substantially similar in sequence and function to SEQ ID NO: 2. The S100B mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

It is an object of the present invention to provide means of expressing a gene, protein, RNA interference molecule or the like in a cell, tissue or organ. As such, the inventors thus provide novel expression vectors comprising S100B mini-promoters which are capable of accomplishing this task. In one embodiment, there is provided an expression vector comprising a S100B mini-promoter, wherein the S100B mini-promoter comprises a S100B regulatory element operably linked in a non-native conformation to a S100B basal promoter. The S100B mini-promoter may have a nucleic acid sequence which is substantially similar in sequence and function to SEQ ID NO:1. The S100B basal promoter may have a nucleic acid sequence which is substantially similar in sequence and function to SEQ ID NO: 2. The S100B regulatory element may have a nucleic acid sequence which is substantially similar in sequence and function to SEQ ID NO: 3. In other embodiments, there is provided an expression vector comprising a S100B mini-promoter, wherein the S100B mini-promoter comprises a S100B basal promoter. The S100B basal promoter may have a nucleic acid sequence which is substantially similar in sequence and function to SEQ ID NO: 2. The S100B mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT, e.g. human HPRT, mouse HPRT, etc.

The inventors have herein demonstrated that expression vectors comprising novel S100B mini-promoter elements are capable of directing transcription of an expression sequence in specific cell types, for instance in glial cells in the brain. In one embodiment of the invention, there is thus provided a method for expressing a gene, protein, RNA interference molecule or the like in a cell, the method comprising introducing into the cell an expression vector comprising a S100B mini-promoter element, wherein the S100B mini-promoter element comprises a S100B regulatory element operably linked in a non-native conformation to a S100B basal promoter element. In another embodiment, the S100B mini-promoter comprises a S100B basal promoter. Cells of interest include, without limitation, cells of the peripheral or central nervous system and progenitors thereof, e.g. embryonic stem cells, neural stem cells, neurons, glial cells, astrocytes, microgial cells, etc. The S100B mini-promoter may have a nucleic acid sequence which is substantially similar in sequence and function to SEQ ID NO: 1. The S100B regulatory element may have a nucleic acid sequence which is substantially similar in sequence and function to SEQ ID NO: 3. The S100B basal promoter may have a nucleic acid sequence which is substantially similar in sequence and function to SEQ ID NO: 2. The S100B mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a S100B mini-promoter element, wherein the S100B mini-promoter element comprises a S100B regulatory element operably linked in a non-native conformation to a S100B basal promoter element, and wherein the expressible sequence comprises a reporter gene. In other embodiments, the S100B mini-promoter comprises a S100B basal promoter. The S100B mini-promoter element may have a nucleic acid sequence substantially similar in sequence and function to SEQ ID NO: 1. The S100B regulatory element may have a nucleic acid sequence substantially similar in sequence and function to SEQ ID NO: 3. The S100B basal promoter element may have a nucleic acid sequence substantially similar in sequence and function to SEQ ID NO: 2. The inventors have demonstrated that expression vectors comprising certain human S100B promoter elements are capable of expression in specific regions of the brain. In some embodiments, the cell is a peripheral or central nervous system cell or progenitors thereof, including, without limitation, embryonic stem cells, neural stem cells, glial cell, neuronal cells, astrocytes, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a cell, the method comprising: 1) introducing into the cell a expression vector comprising a S100B mini-promoter element operably linked to an expressible sequence, wherein the S100B mini-promoter element comprises a S100B regulatory element operably linked in a non-native conformation to a S100B basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the S100B mini-promoter comprises a S100B basal promoter. The S100B mini-promoter element may have a nucleic acid sequence substantially similar in sequence and function to SEQ ID NO: 1. The S100B regulatory element may have a nucleic acid sequence substantially similar in sequence and function to SEQ ID NO: 3. The S100B basal promoter element may have a nucleic acid sequence substantially similar in sequence and function to SEQ ID NO: 2. In such a fashion, one may be able to follow the development of a parent cell as it differentiates into more mature cells. As an example, one could introduce an expression vector comprising the aforementioned S100B mini-promoter elements into a pluripotent stem cell, monitor the expression of the reporter gene that is being expressed by the S100B promoter elements during the maturation and differentiation of the stem cell and thus determine the state of maturation, for instance in the differentiation of the pluripotent stem cell into a specific brain cell type. The inventors have demonstrated that the S100B mini-promoter elements described herein direct transcriptional expression in certain brain cell types, and so detection of reporter gene expression in a cell would thus be indicative of the cellular identity of the cell as being a certain type of brain cell.

The inventors have herein demonstrated that certain S100B mini-promoter elements of the present invention are capable of driving expression in the glia cells of the cerebellum, cortex and hippocampus regions of the brain and in glial cells in the eye. This surprising expression pattern provides additional methods of use for these mini-promoter elements. For instance, it may be desirable to utilize the S100B mini-promoters of the present invention in a gene therapy or cell therapy application wherein the S100B mini-promoters are utilized to drive expression of a therapeutic or beneficial compound, such as a protein, in glial cells. In such a way, the therapeutic or beneficial compound may be useful for a disease or condition that involves such glial cells, involves expression of a therapeutic molecule in the thalamus, or which may be improved by expression of the therapeutic or beneficial compound in those cells or other supporting cells in the central nervous system. In certain embodiments of the invention, there is thus provided a method of treatment of a subject having a disease involving glial cells, the method comprising administering to the subject a therapeutically effective dose of a composition comprising a S100B mini-promoter element, wherein the S100B mini-promoter element comprises a S100B regulatory element operably linked in a non-native conformation to a S100B basal promoter element. In another embodiment, the S100B mini-promoter comprises a S100B basal promoter. The S100B mini-promoter element may have a nucleic acid sequence substantially similar in sequence and function to SEQ ID NO: 1. The S100B regulatory element may have a nucleic acid sequence substantially similar in sequence and function to SEQ ID NO: 3. The S100B basal promoter element may have a nucleic acid sequence substantially similar in sequence and function to SEQ ID NO: 2. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy, neuroinflammation, astrogliosis, multiple sclerosis, Parkinson's disease, Alzheimer's disease, aging, traumatic brain injury.

The inventors herein further describe the present invention by way of the following non-limiting examples:

EXPERIMENTAL

Virus Generation and Analysis
Virus Production

Figure 1:
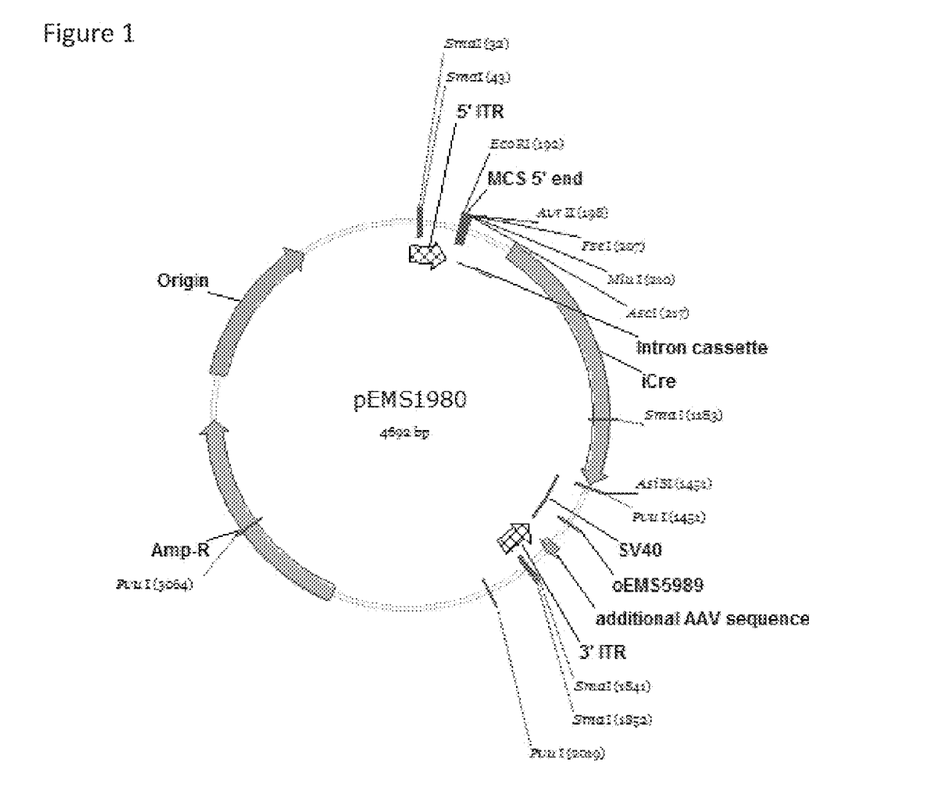
FIG. 1—Viral expression vector (pEMS1980) into which S100B promoter elements could be inserted for expression studies. The S100B promoter with a nucleic acid sequence corresponding to SEQ ID NO: 1 (Ple266) was inserted into the multiple cloning site (MCS) of the pEMS1980 backbone vector such that it became operably linked to the iCre reporter gene.

The Ple266 MiniPromoter were generated by direct synthesis by DNA2.0 (Menlo Park, Calif., USA) (SEQ ID NO: 1). The mini-promoter was into the pEMS1980 backbone (FIG. 1), containing the iCre reporter, using Avrll and Ascl restriction enzymes. One μg of pEMS1994 plasmid containing the Ple266 MiniPromoter was prepared by miniprep and sent to the Vector Core at the University of Pennsylvania (Philadelphia, Pa., USA) to be made into AAV9 serotype virus.

Virus Injection

B6-Gt(ROSA26)$^{tm1Sor}$ females were crossed to 129-Gt(ROSA26)$^{tm1Sor}$ to yield hybrid F1 homozygous pups for injecting virus. Plug checks were performed on the females such that the day of birth could be accurately estimated. P0 pups were used for virus injections. If the female gave birth in the morning, virus was injected in the afternoon. If she gave birth in the afternoon, virus was injected the next morning. A standard injection into the superficial temporal vein of a newborn pup was performed using $1\times10^{13}$ GC/mL (genome copies per milliliter) virus in a total volume of 50 μL (in PBS) with a 30 gauge needle and a 1 cc syringe. After injections, pups were tattooed for identification and returned to their cage.

Harvesting of Animals

Virus-injected mice were harvested at P21 or P56 (postnatal day 21 or 56). Animals were given a lethal dose of avertin injected intraperitoneally. Thereafter perfusion with 1×PBS for 2 minutes and 4% PFA/PBS for 8 minutes was performed. Tissues were harvested and post-fixed for 1 hour at 4° C. The tissues were then stored in 0.02% Azide/PBS at 4° C.

Histology

Tissues were cryoprotected in 30% sucrose/PBS overnight at 4° C. After embedment in OCT the following day, 20 μm sections were directly mounted onto slides. For X-gal staining, tissues were rinsed in PBS and Triton-X/PBS and stained in 0.1% X-gal solution overnight at 30-35° C. After staining sections were rinsed and counterstained with neutral red, dehydrated and mounted with coverslips. For co-labeling of X-gal with markers using immunohistochemistry, standard IHC procedure was followed and the X-gal stain was performed either prior to primary antibody incubation or between primary and secondary antibodies, depending on the strength of the X-gal stain. X-gal stains blue any cells that have recombined the Gt(ROSA26)$^{tm1Sor}$ locus due to iCre recombinase activity and thus expressing the β-galactosidase protein.

Example 1

Expression of Reporter in Brain and Eye by the Ple266 Mini-Promoter Construct

The Ple266 construct was tested in recombinant single-stranded adeno-associated virus serotype 9 (rAAV9 or ssAAV9) driving the iCre recombinase reporter. Mice were injected intravenously with virus at post-natal day 0 (P0) as described elsewhere (Foust et al. 2009. Nat Biotech. 27:59-65). Expression was analyzed P21 and P56 via recombination of the reporter locus Gt(ROSA26)Sor$^{tmSor1}$ (Soriano 1999. Nat Genetics: 21:70-71). Once recombined, this locus expressed the β-galactosidase (lacZ gene) enzyme. Histochemical reaction with the X-gal substrate results in blue signal where the reporter is expressed.

Figure 2A:
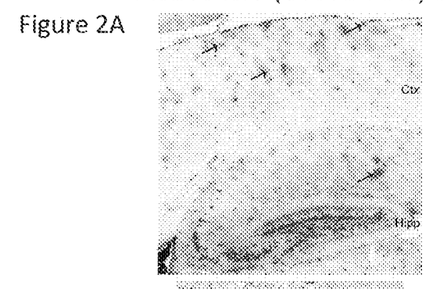
Figure 2B:
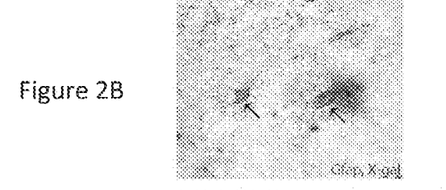
Figure 2C:
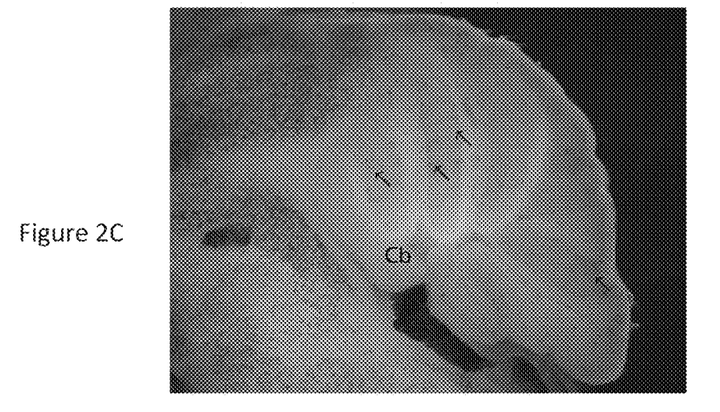
Figure 2D:
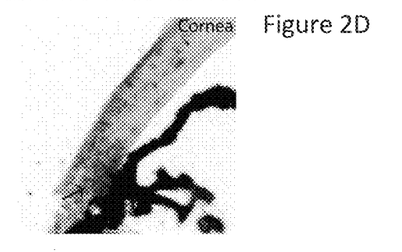
Figure 2E:
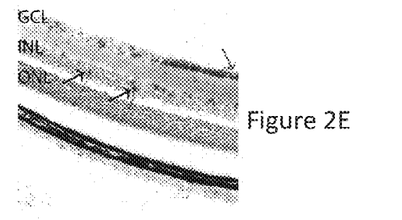

As shown in FIG. 2A-2C, there was strong staining that co-localized with astrocyte markers in the glia cells of the cerebellum, cortex and hippocampus. Expression was also observed in the eye (FIG. 2D), in particular within the Muller glia cells of the retina (FIG. 2E).

What is claimed is:

1. An isolated polynucleotide comprising a S100B mini-promoter wherein the S100B mini-promoter comprises a S100B regulatory element with at least 99% sequence identity to SEQ ID NO: 3 operably joined to a S100B basal promoter with at least 99% sequence identity to SEQ ID NO: 2 through a non-native spacing of not more than 500 nucleotides between the regulatory element and the basal promoter.

2. The isolated polynucleotide of claim 1, comprising a S100B mini-promoter with at least 99% sequence identity to SEQ ID NO: 1.

3. The isolated polynucleotide of claim 1, operably linked to an expressible sequence.

4. A vector comprising the isolated polynucleotide of claim 1.

5. An isolated cell comprising the vector of claim 4.

6. The cell of claim 5, wherein the vector is stably integrated into the genome of the cell.

7. The cell of claim 5, wherein the cell is a stem cell, a retinal cell, a retinal progenitor, a neural stem cell or a neural progenitor cell.

8. An isolated polynucleotide comprising a S100B mini-promoter wherein the S100B mini-promoter comprises a S100B regulatory element with at least 95% sequence identity to SEQ ID NO: 3 operably joined to a S100B basal promoter with at least 95% sequence identity to SEQ ID NO: 2 through a non-native spacing of not more than 500 nucleotides between the regulatory element and the basal promoter.

9. The isolated polynucleotide of claim 8, wherein the S100B mini-promoter has at least 95% sequence identity to SEQ ID NO: 1.

10. The isolated polynucleotide of claim 8, operably linked to an expressible sequence.

* * * * *